(12) United States Patent
Koivusalmi et al.

(10) Patent No.: US 7,850,841 B2
(45) Date of Patent: Dec. 14, 2010

(54) PROCESS FOR PRODUCING A BRANCHED HYDROCARBON BASE OIL FROM A FEEDSTOCK CONTAINING ALDEHYDE AND/OR KETONE

(75) Inventors: Eija Koivusalmi, Kulloonkylä (FI); Ilkka Kilpeläinen, Kulloonkyulä (FI); Pirkko Karhunen, Espoo (FI); Jorma Matikainen, Helsinki (FI)

(73) Assignee: Neste Oil Oyj, Espoo (FI)

( * ) Notice: Subject to any disclaimer, the term of this patent is extended or adjusted under 35 U.S.C. 154(b) by 399 days.

(21) Appl. No.: 11/637,139

(22) Filed: Dec. 12, 2006

(65) Prior Publication Data

US 2007/0135316 A1    Jun. 14, 2007

Related U.S. Application Data

(60) Provisional application No. 60/749,035, filed on Dec. 12, 2005.

(51) Int. Cl.
*C10M 101/00* (2006.01)
*C10M 177/00* (2006.01)
*C10G 71/00* (2006.01)

(52) U.S. Cl. .............................. 208/64; 208/18; 208/63; 568/312; 568/388; 568/463; 508/216

(58) Field of Classification Search .................... 208/18, 208/19, 133, 62, 63, 64, 66; 508/216, 217; 536/125; 560/203; 568/310, 312, 313, 383, 568/384, 388, 390, 463, 464
See application file for complete search history.

(56) References Cited

U.S. PATENT DOCUMENTS

| | | | |
|---|---|---|---|
| 3,182,017 A | 5/1965 | Fleck et al. | |
| 3,242,080 A | 3/1966 | Wiley et al. | |
| 3,444,143 A | 5/1969 | Morris et al. | |
| 3,501,546 A | 3/1970 | Dubeck | |
| 4,026,960 A | 5/1977 | Nishida | |
| 4,133,841 A | 1/1979 | Cosyns et al. | |
| 4,299,979 A | 11/1981 | Murphy | |
| 4,317,948 A | 3/1982 | Heckelsberg | |
| 4,457,944 A | 7/1984 | Conrad et al. | |
| 4,744,884 A | 5/1988 | Moorehead et al. | |

(Continued)

FOREIGN PATENT DOCUMENTS

DE    1024238 B    2/1958

(Continued)

OTHER PUBLICATIONS

Schaper, U.-A., "Die gemischte Guerbet-Reaktion zwischen cyclishen und acyclischen Alkoholen," Fette, Seifen, Anstrichmittel, 1980, vol. 82, No. 11, 454-456.

(Continued)

*Primary Examiner*—Walter D Griffin
*Assistant Examiner*—Renee Robinson
(74) *Attorney, Agent, or Firm*—Birch, Stewart, Kolasch and Birch, LLP

(57) ABSTRACT

The invention relates to a process for producing high-quality hydrocarbon base oil particularly of biological origin. The process of the invention comprises aldol condensation, hydrodeoxygenation, and isomerization steps. Aldehydes and/or ketones, preferably of biological origin are used as the feedstock.

15 Claims, 1 Drawing Sheet

U.S. PATENT DOCUMENTS

Figure 1:
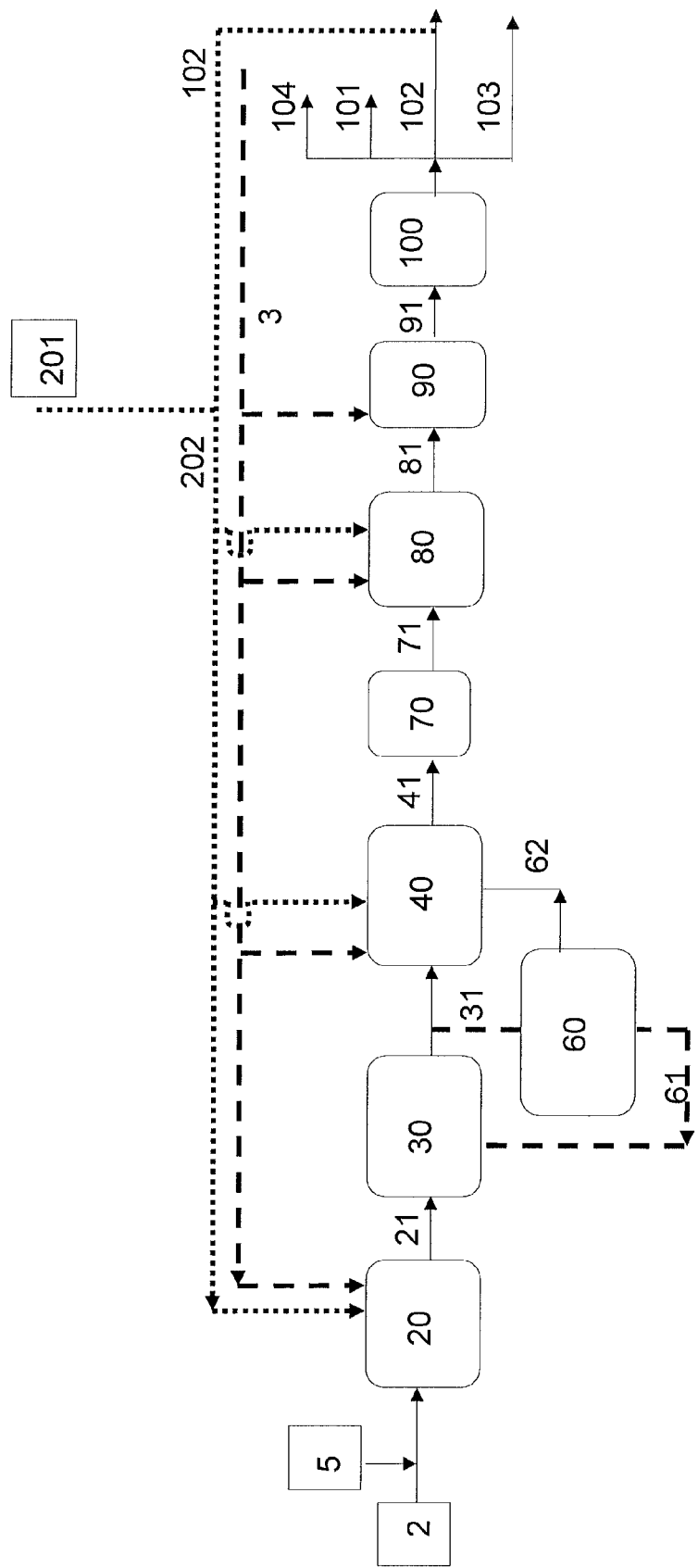

| | | | |
|---|---|---|---|
| 4,783,274 | A | 11/1988 | Jokinen et al. |
| 5,333,698 | A | 8/1994 | Van Slyke |
| 5,416,239 | A | 5/1995 | Westfechtel et al. |
| 5,444,170 | A | 8/1995 | Vedage |
| 5,516,960 | A | 5/1996 | Robinson |
| 5,705,722 | A | 1/1998 | Monnier et al. |
| 5,719,097 | A | 2/1998 | Chang et al. |
| 6,245,725 | B1 | 6/2001 | Tanaka et al. |
| 6,562,230 | B1 | 5/2003 | O'Rear et al. |
| 6,599,864 | B1 | 7/2003 | Bertomeu |
| 6,683,224 | B1 | 1/2004 | Hourticolon |
| 6,703,356 | B1 | 3/2004 | Wu |
| 2002/0062055 | A1 | 5/2002 | Raulo et al. |
| 2003/0181769 | A1 | 9/2003 | Both et al. |
| 2004/0002620 | A1* | 1/2004 | Schwerin et al. ............ 568/471 |
| 2004/0053796 | A1 | 3/2004 | O'Rear |
| 2004/0055209 | A1 | 3/2004 | Jakkula et al. |
| 2004/0099571 | A1 | 5/2004 | Germaine et al. |
| 2004/0230085 | A1 | 11/2004 | Jakkula |
| 2005/0077209 | A1 | 4/2005 | Miller et al. |
| 2005/0133408 | A1 | 6/2005 | Abernathy et al. |
| 2005/0241990 | A1 | 11/2005 | Ziemer et al. |
| 2006/0027486 | A1 | 2/2006 | Rosenbaum et al. |

FOREIGN PATENT DOCUMENTS

| | | |
|---|---|---|
| DE | 33407111 | 9/2004 |
| DE | 33407111 A1 | 9/2004 |
| EP | 0 209 997 A1 | 1/1987 |
| EP | 209997 | 1/1987 |
| EP | 0 457 665 A1 | 11/1991 |
| EP | 0 591 297 A1 | 4/1994 |
| EP | 0 774 451 A1 | 5/1997 |
| EP | 1396531 A2 | 3/2004 |
| EP | 1 681 337 A1 | 7/2006 |
| EP | 1681337 A1 | 7/2006 |
| FI | 66899 B | 8/1984 |
| FI | 100248 A | 8/1997 |
| FI | 1100248 | 10/1997 |
| FR | 579 601 A | 10/1924 |
| GB | 175974 | 6/1923 |
| GB | 175974 A | 6/1923 |
| GB | 1193220 A | 5/1970 |
| GB | 1524781 A | 9/1978 |
| JP | 01056792 | 3/1989 |
| JP | 01056792 A | 3/1989 |
| WO | WO-93/00320 A1 | 1/1993 |
| WO | WO-96/17902 A1 | 6/1996 |
| WO | WO 2004/062763 | 7/2004 |
| WO | WO-2004/062763 A2 | 7/2004 |

OTHER PUBLICATIONS

Ulmanns, Encykolpadie der technischen Chemie, 4., neubearbeitete und erweiterte Auflage, Band 13, (1976), Verlag Chemie GmbH, Weinheim, p. 146.

Morrison, R.T. and Boyd, R.N., Organic Chemistry, 5$^{th}$ ed. (1987), Allyn and Bacon, Newton, Massachusetts, pp. 94, 640, 679-680, 913-914.

Kirk-Othmer, Encyclopedia of Chemical Technology, 3$^{rd}$ ed., (1980), vol. 9, Wiley, p. 370.

Cui, S.T., et al., "Nonequilibrium Molecular Dynamics Simulation of the Rheology of Linear and Branched Alkanes", International Journal of Thermophysics, 1988, vol. 19, No. 2, pp. 449-459.

English translation of Finnish Patent Office Search Report for Finnish Patent Application No. FI200556665.

Burg, et al., JAOCS, (1991), vol. 68, (8), pp. 600-603.

Cui, S.T., et al., "Nonequilibrium Molecular Dynamics Simulation of the Rheology of Linear and Branches Alkanes", International Journal of Thermophysics, 1988, vol. 19, No. 2, pp. 449-459.

English translation of Finnish Patent Office Search Report for Finnish Patent Application No. FI-200556665.

Kirk-Othmer, Encyclopedia of Chemical Technology, 3rd ed., (1980), vol. 7, Wiley, p. 768.

Klimkiewicz et al., "Ketonization of long chain esters from transesterification of technical waste fats", J. Chem. Technol. Biotechnol. vol. 76, 2001, pp. 35-38.

Koster, R.M., et al., Active sites in the clay catalysed dimerisation of oleic acid, Journal of Molecular Catalysis A: Chemical, (1998), vol. 134, pp. 159-169.

Laurent, E., et al., Study of the hydrodeoygenation of carbonyl, carboxylic and guaiacyl groups over sulfided CoMo/ $\gamma$-Al$_2$O$_3$ and NiMo/ $\gamma$-Al$_2$O$_3$ catalyst. II. Influence of Water, ammonia and hydrogen sulfide, Applied Catalysis A, (1994), vol. 109. pp. 97-115.

Laurent, E., et al., Study of hydrodeoygenation of carbonyl, carboxylic and guaiacyl groups over sulfided CoMo/ $\gamma$-Al$_2$O$_3$ and NiMo/ $\gamma$-Al$_2$O$_3$ catalyst. I. Catalytic reaction schemes, Applied Catalysus A, (1994), vol. 109, pp. 77-96.

Maier, W.F. et al., Gas Phase Decarboxylation of Carboxylic Acids, Chem. Ber., (1982), vol. 115, pp. 808-812.

Morrison, R.T. and Boyd, R. N., Organic Chemistry, 5th ed. (1987), Allyn and Bacon, Newton, Massachusetts, pp. 94, 640, 679-680, 913-914.

Notification of Transmittal of the International Search Report and Written Opinion of the International Searching Authority for PCT/FI2006/050553.

Schaper, U.-A., "Die gemischte Guerbet-Reaktion zwischen cyclishen und acyclischen Alkoholen," Fette, Seifen, Anstrichmittel, 1980, vol. 82, No. 11, 454-456.

"Scope of Accreditation for Testing" 2009.

Translation of Search Report of FI-20055661 dated May 12, 2006.

Ulmanns, Encykolpadie der technischen Chemie, 4., neubearbeitete und erweiterte Auflage, Band 13, (1976), Verlag Chemie GmbH, Weinheim, p. 146.

Ullmanns Encyklopadie der technischen Chemie, 4., neubearbeitete und erweiterte Auflage, Band 13, Verlag Chemie GmbH, Weinheim 1983, Hydruerung p. 140.

Office Action issued in U.S. Appl. No. 11/636,567 on Jan. 27, 2009.

Office Action issued in U.S. Appl. No. 11/636,567 on Aug. 18, 2009.

Office Action issued in U.S. Appl. No. 11/637,139 on Apr. 6, 2009.

Office Action issued in U.S. Appl. No. 11/637,107 on Apr. 6, 2009.

Office Action issued in U.S. Appl. No. 11/637,107 on Dec. 14, 2009.

Office Action issued in U.S. Appl. No. 11/637,159 on Mar. 11, 2010.

Search report from PCT/FI2006/050548.

Ullmanns Encyklopadie der technischen Chemie, 4., neubearbeitete und erweiterte Auflage, Band 13, Verlag Chemie GmbH, Weinheim 1983, Hydrierung p. 140.

Office Action dated Aug. 6, 2010 issued in U.S. Appl. No. 11/636,567.

Office Action dated Aug. 6, 2010 issued in U.S. Appl. No. 11/637,107.

Examiner Interview Summary and Notice of Allowance dated Jul. 1, 2010 issued in U.S. Appl. No. 11/637,159.

Office Action dated Aug. 25, 2010 in U.S. Appl. No. 12/433,394.

* cited by examiner

PROCESS FOR PRODUCING A BRANCHED HYDROCARBON BASE OIL FROM A FEEDSTOCK CONTAINING ALDEHYDE AND/OR KETONE

This Non-provisional application claims priority under 35 U.S.C. §119(e) on U.S. Provisional Application No(s). 60/749,035 filed on Dec. 12, 2005, the entire contents of which are hereby incorporated by reference.

TECHNICAL FIELD

The invention relates to a process for producing a hydrocarbon component, and particularly a process for producing high-quality branched saturated hydrocarbon component of biological origin to be used as new type base oil. The process comprising aldol condensation, hydrodeoxygenation and isomerization steps utilizes feedstock, which preferably originates from raw material of biological origin, eventually derived from plant oils, animal fats, natural waxes, and carbohydrates. Also corresponding synthetic materials and combinations thereof may be used as feedstock.

PRIOR ART

Base oils are commonly used for the production of lubricants, such as lubricating oils for automotives, industrial lubricants and lubricating greases. They are also used as process oils, white oils and metal working oils. Finished lubricants consist of two general components, lubricating base oil and additives. Lubricating base oil is the major constituent in these finished lubricants and contributes significantly to the properties of the finished lubricant. In general, a few lubricating base oils are used to manufacture a wide variety of finished lubricants by varying the mixtures of individual lubricating base oils and individual additives.

Base oils according to the classification of the American Petroleum Institute (API) Group III or IV are used in high-quality lubricants. API base oil classification is shown in Table 1.

TABLE 1

API base oil classification

| Group | Saturated hydrocarbons, wt-% (ASTM D 2007) | Sulfur, wt-% (ASTM D 1552/ D 2622/D 3120/ D4294/D 4927) | Viscosity index (VI) (ASTM D 2270) |
|---|---|---|---|
| I | <90 and/or | >0.03 | $80 \leq VI < 120$ |
| II | $\geq 90$ | $\leq 0.03$ | $80 \leq VI < 120$ |
| III | $\geq 90$ | $\leq 0.03$ | $\geq 120$ |
| IV | All polyalphaolefins (PAO) | | |
| V | All other base oils not belonging to Groups I-IV | | |

Oils of the Group III are base oils with very high viscosity indices (VHVI) produced by modern methods from crude oil by hydrocracking, followed by isomerization of the waxy linear paraffins to give branched paraffins. Oils of Group III also include base oils produced from Slack Wax paraffins from mineral oils, and from waxes obtained by Fischer-Tropsch synthesis (GTL waxes) for instance from coal or natural gas using corresponding isomerization techniques. Oils of Group IV are synthetic polyalphaolefins (PAO). A similar classification is also used by ATIEL (Association Technique de l'Industrie Européenne desi Lubrifiants, or Technical Association of the European Lubricants Industry), said classification also comprising Group VI: Polyinternalolefins (PIO). In addition to the official classification, also Group II+ is commonly used in this field, this group comprising saturated and non-sulfurous base oils having viscosity indices of more than 110, but below 120. In these classifications saturated hydrocarbons include paraffinic and naphthenic compounds, but not aromatics.

There is also available a definition for base stocks according to API 1509: "A base stock is a lubricant component that is produced by a single manufacturer to the same specifications (independent of feed source or manufacturer's location); that meets the same manufacturer's specification; and that is identified by a unique formula, product identification number, or both. Base stocks may be manufactured using a variety of different processes". Base oil is the base stock or blend of base stocks used in API-licensed oil. The base stock types are 1) Mineral oil (paraffinic, naphthenic, aromatic), 2) Synthetic (polyalphaolefins, alkylated aromatics, diesters, polyol esters, polyalkylene glycols, phosphate esters, silicones), and 3) Plant oil.

Already for a long time, especially the automotive industry has required lubricants and thus base oils with improved technical properties. Increasingly, the specifications for finished lubricants require products with excellent low temperature properties, high oxidation stability and low volatility. Generally lubricating base oils are base oils having kinematic viscosity of about 3 cSt or greater at 100° C. (KV100); pour point (PP) of about −12° C. or less; and viscosity index (VI) about 100 or greater. In general, lubricating base oils should have a Noack volatility no greater than current conventional Group I or Group II light neutral oils.

It is no longer possible to produce lubricants complying with the specifications of the most demanding car manufacturers from conventional mineral oils. Typically, mineral oils often contain too high concentrations of aromatic, sulfur, and nitrogen compounds, and further, they also have a high volatility and a modest viscosity index, that is, viscosity-temperature dependence. Moreover, response of mineral oils to antioxidant additives is often low. Synthetic and so-called semi-synthetic base oils play an increasingly important role especially in automotive lubricants, such as in engine and gear oils. A similar development can be seen for industrial lubricants. Service life of lubricants is desirably as long as possible, thus avoiding frequent oil changes by the user, and further allowing extended maintenance intervals of vehicles for instance in commercial transportation. In the past decade, engine oil change intervals for passenger cars have increased five fold, being at best 50,000 km. For heavy-duty vehicles, engine oil change intervals are at present already on the level of 100,000 km.

Production of lubricants is influenced by increasingly common "Life Cycle Approach" (LCA) concerning environment, health and safety factors of the product. What is aimed with LCA are an extended service life of the product, and minimal drawbacks to the environments associated with the production, use, handling and disposal of the product. Longer oil change intervals of high-quality base oils result in decreased consumption of non-renewable mineral crude oil based raw materials, and lower amounts of hazardous waste oil products.

In addition to the demands for engine technology and base oil production, also strict environmental requirements direct the industry to develop more sophisticated base oils. Sulfur free fuels and base oils are required in order to gain full effect of new and efficient anti-pollution technologies in modern vehicles and to cut emissions of nitrogen oxides, volatile hydrocarbons and particles, as well as to achieve direct reduction of sulfur dioxide in exhaust gases. The European Union has decided that these fuels shall be available to the market from 2005 and they must be the only form on sale from 2009. Conventional mineral oil base oils contain sulfur, nitrogen, aromatic compounds, and typically also volatile compounds. They are less suitable for new engines and thus also environmentally more detrimental than newer sulfur and aromatic free base oils.

Nowadays, the use of recycled oils and renewable raw materials in the production of lubricants is frequently an object of interest. The use of renewable raw materials of biological origin instead of non-renewable fossil raw materials to produce hydrocarbon components is desirable, because the fossil raw materials are exhaustible and their effect on environment is detrimental. Problems associated with recycled oils include complicated purification and reprocessing steps to obtain base oils with high quality. Further, the development of a functioning and extensive recycling logistic system is expensive.

For the time being, only esters are used in lubricants of renewable and biological origin. The use of said esters is limited to a few special applications such as oils for refrigeration compressor lubricants, bio-hydraulic oils and metal working oils. In normal automotive and industrial lubricants, they are used mainly in additive scale. Also high price limits the use of esters. In addition, the esters used in engine oil formulations are not interchangeable with other esters without performing new engine tests, even in cases where the chemical composition of the substituting ester is in principle similar. Instead, base oils consisting of pure hydrocarbon structure are partly interchangeable with each other. There are also some technical problems associated with esters. As polar compounds, esters suffer greater seal-swelling tendency than pure hydrocarbons. This has created lot of problems relating to elastomers in hydraulic applications. In addition, ester base oils are hydrolyzed more easily producing acids, which in turn cause corrosion on lubricating systems. Further, even greater disadvantage of esters is that additives developed for non-polar hydrocarbon base oils are not effective for ester base oils.

Processes for producing unsaturated and branched aldehydes having longer hydrocarbon chains are available starting from aldehydes and ketones using aldol condensation reaction. The reaction proceeds through aldol condensation to give hydroxy aldehyde, or hydroxy ketone, followed by cleavage of water yielding unsaturated aldehyde or unsaturated ketone, depending on feed. In the reaction, typically basic catalysts are used at a temperature of 80 to 400° C. Basic homogeneous catalysts such as NaOH and $Ca(OH)_2$, and supported alkali metals like $Na/SiO_2$ may be mentioned as heterogeneous catalysts, as described by Kelly, G. J. et al., Green Chemistry, 2002, 4, 392-399. Ion exchange resins containing quaternary ammonium groups may be used as catalyst only when low carbon number feed is condensed, because the resin cannot be used at high temperatures.

Fatty alcohols may be produced by hydrogenation of either fatty acids or fatty acid alkyl esters. Three types of hydrogenation units for producing alcohols from alkyl esters are in commercial use: gas phase hydrogenation, trickle-bed hydrogenation, and suspension hydrogenation. Of these, the first two comprise a fixed bed catalyst. In all processes, a catalyst containing copper chromite is used at a temperature of 200 to 250° C. and under a pressure of 20 to 30 MPa. Unsaturated fatty alcohols are produced using copper-zinc catalysts containing no chromium. Moreover, saturated alcohols may also be produced at 200 to 230° C., under a pressure of about 20 MPa using a nickel catalyst activated with chromium, iron, or rhodium.

Fatty aldehydes may be produced from fatty alcohols by removing hydrogen in a dehydrogenation reaction. The reaction is opposite to the hydrogenation reaction of alcohols, and thus endothermic. In the dehydrogenation reaction, corresponding hydrogenation catalysts are used but the temperature is higher, and thus side reactions such as cracking, isomerization, cyclization, and polymerization are possible. Supported copper chromite catalysts are typically used for producing aldehydes from alcohols. In gas phase dehydrogenation, typically temperatures between 250 and 400° C., and pressures between 0.1 and 0.5 MPa are used. Moreover, it is generally known that corresponding aldehydes can be produced from alcohols using alumina, silica-alumina, hafnium oxide and zirconium oxide as catalyst. The products of the process are controlled by changing process temperature. At low temperatures ethers are obtained, high temperatures give aldehydes, whereas olefins are typically obtained at 300-350° C.

Processes for producing ketones are known in the art where the functional groups of the feed molecules react with each other forming a ketone. The carbon number of the ketone formed is reduced by one compared to the sum of the carbon numbers of the reacted feed molecules. Metals or oxides of alkaline earth metals are used as catalysts. EP 591297 describes a method for producing a ketone from fatty acids by pyrolysis reaction using magnesium oxide catalyst. EP 0457665 discloses a method for producing ketones from triglycerides, fatty acids, fatty acid esters, fatty acid salts, and fatty acid anhydrides using bauxite catalyst containing iron oxide.

Aldehydes and ketones, other than of fatty acid origin, may be prepared from carbohydrates by acid hydrolysis of biomass. The major constituents of the biomass, of hemicellulose are pentosans (C5 carbohydrates) and of cellulose are hexosans (C6 carbohydrates), which when hydrolyzed yield C5 sugars (pentoses) and C6 sugars (hexoses). The carbonyl groups in sugars are mainly aldehyde and only a few are ketones. 5-carbon sugars degrade more rapidly than 6-carbon sugars, and one way to decrease sugar degradation in acid hydrolysis is to have a two-stage process. The first stage is conducted under mild process conditions to recover the 5-carbon sugars while the second stage is conducted under harsher conditions to recover the 6-carbon sugars. Sugars are reacted further in the presence of a mineral acid catalyst to yield corresponding aldehydes or ketones. There are two basic types of acid processes: dilute acid and concentrated acid, again with variations of each process. Dilute acid processes are conducted under high temperatures of 160-300° C. and pressure, and have reaction times in the range of seconds or minutes, which facilitates continuous processing.

FI 100248 presents a process with two steps wherein middle distillate is produced from plant oil by hydrogenation of the carboxylic acids or triglycerides of said plant oil to yield linear normal paraffins, followed by isomerization of said n-paraffins to give branched paraffins. The hydrogenation was performed at a temperature ranging from 330 to 450° C., under a pressure of higher than 3 MPa and the liquid hourly space velocity (LHSV) being from 0.5 to 5 l/h. The isomerization step was carried out at 200 to 500° C., under elevated pressure, and LHSV being from 0.1 to 10 l/h.

EP209997 discloses a process for producing base oils by isomerization of waxy hydrocarbons derived from crude oil, thus producing only low amounts of light fractions. This method is used for instance for producing base oils of Group III from the waxy hydrocracking bottom oils.

Starting materials from biological sources contain high amounts of oxygen. In processing oxygen is converted to water, carbon monoxide, and carbon dioxide. In addition, starting materials of biological origin often contain nitrogen, sulfur and phosphorus known as catalyst poisons and inhibitors of noble metal catalysts. They cause decreased service life of the catalyst and make frequent regeneration of the catalysts necessary. In base oil processes, normal paraffins are often isomerized to obtain branches in the hydrocarbon chain, said branches improving low temperature properties. Noble metal catalysts are used in isomerization processes. They are very expensive and highly sensitive to catalyst poisons.

A process utilizing starting materials or intermediates of biological origin, containing heteroatoms, said starting materials being optionally subjected to thermal and/or chemical and/or physical and/or mechanical pre-treatment steps, for producing high-quality base oils is so far not disclosed.

On the basis of the above teachings it may be seen that there is an obvious need for an alternative process for producing branched saturated hydrocarbon components preferably from starting materials of biological origin, said process contributing to avoiding, or at least substantially reducing problems associated with the solutions of the prior art.

There is also an obvious need for branched, non-polar paraffinic base oils complying with the quality requirements for high-quality base oils, said base oil being preferably of biological origin and having more preferable impacts on the environment and for end users than traditional mineral base oils. In addition, there is a need for a process based on the use of renewable feedstock, thus saving non-renewable raw materials.

OBJECTS OF THE INVENTION

An object of the invention is a process for producing a hydrocarbon component.

A further object of the invention is a process for producing a hydrocarbon component using starting materials of biological origin.

Another object of the invention is a process for producing base oils.

Still another object of the invention is a process for producing a new type of branched paraffinic base oils not containing heteroatoms, from starting materials of biological origin.

An object of the invention is moreover a base oil complying with the requirements of the API Group III.

The characteristic features of the process and base oils of the invention are presented in the appended claims.

GENERAL DESCRIPTION OF THE INVENTION

The process of the invention comprises a condensation step of aldehydes and ketones. Preferably of the aldehydes and ketones are derived from fatty acids or carbohydrates. The reaction in presented in scheme I below, wherein molecules of the feedstock react with each other, thus increasing the carbon chain length of the branched component thus obtained. Further, the process of the invention comprises a hydrodeoxygenation step for removing heteroatoms from the condensation product, and finally, an isomerization step for making branches to the molecular structure and thus improving low temperature properties of the paraffinic product.

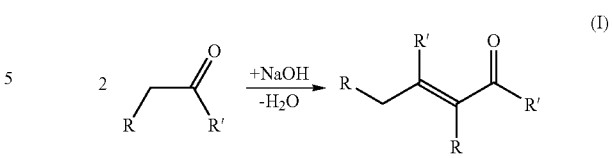

where, R'=H (aldehyde), or C3-C23 (ketone);
and R=C2-C22.

Preferably feedstocks originating from starting materials of biological origin are primarily used. In addition, the process may comprise optional prehydrogenation, finishing, and product recirculation steps.

The aldol condensation reaction is utilized for increasing the hydrocarbon chain length of the feed stream to obtain a product being an unsaturated branched monofunctional carbonyl compound.

Here, carbonyl compound refers to a compound containing carbonyl functionality of aldehydes or ketones.

Here, fatty acids refer to carboxylic acids of biological origin having a carbon number higher than C1.

Aldehydes and ketones derived from fatty acids; and fatty aldehydes and fatty ketones refer here to aldehydes and ketones obtained from fatty acids or triglycerides of biological origin.

Here, hydrodeoxygenation (HDO) refers to oxygen removal from a compound by means of hydrogen. Water is liberated in the reaction, and simultaneously olefinic double bonds are hydrogenated and any sulfur and nitrogen compounds are removed. Reactions of the HDO step are exothermal. After the HDO step, the structure of the starting material has become paraffinic.

Here, saturated base oil comprises saturated hydrocarbons. The term "saturated hydrocarbons" refers to paraffinic and naphthenic compounds, but not to aromatics. Paraffinic compounds may either be branched or linear. Naphthenic compounds are cyclic saturated hydrocarbons, or cycloparaffins, typically derived from cyclopentane or cyclohexane. A naphthenic compound may comprise a single ring structure (mononaphthene) or two isolated ring structures (isolated dinaphthene), or two fused ring structures (fused dinaphthene) or three or more fused ring structures (polycyclic naphthenes or polynaphthenes).

In this context, width of the carbon number range refers to the difference of the carbon numbers of the largest and the smallest molecules, plus one, in the final product.

In this context, pressures are gauge pressures relative to normal atmospheric pressure.

Classification of the Periodic System of the Elements is the IUPAC classification.

FIGURE

The invention is now illustrated with the appended FIG. 1 without wishing to limit the scope of the invention to the embodiments of said FIGURE.

In FIG. 1, the feedstock stream 2 comprising aldehydes and/or ketones derived from fatty acids or carbohydrates and a hydrogen stream 3 are introduced into a prehydrogenation reactor 20 for the optional prehydrogenation of double bonds. In the prehydrogenation reactor 20 may optionally added part of the lighter product fraction (102) to be recirculated, or another hydrocarbon stream 201 to dilute the feed. The diluent stream 202 comprises the recirculated stream 102, or hydrocarbon stream 201, or a mixture thereof. From said prehydrogenation reactor 20, the saturated aldehyde and/or ketone product is passed as the stream 21 to an aldol condensation reactor 30. Alternatively, other aldehydes 5 such as aldehydes produced synthetically may be introduced into the process either alone or in combination with the above aldehydes. The hydroxy carbonyl compound or preferably alpha, beta-unsaturated carbonyl compound obtained as the product from the aldol condensation reactor 30 is passed as stream 31, whereas hydrogen is passed as stream 3 to the HDO reactor 40. Alternatively, the components not condensed in the condensation reaction, still present in stream 31, may be separated for instance by distillation in a distillation unit 60, followed by recirculation as stream 61 to the aldol condensation reactor 30. The condensed components are passed as stream 62 to the HDO reactor 40. The branched paraffinic product from the HDO step is passed as stream 41 to stripping 70 for removing unwanted impurities. Thereafter, the paraffinic product stream 71 and hydrogen stream 3 is introduced into the hydroisomerization reactor 80, said reactor also optionally receiving a diluent 202. Following hydroisomerization 80, the branched paraffins 81 may be optionally subjected to finishing 90 using a hydrogen stream 3, followed by passing the product as stream 91 to a distillation and/or separation unit 100. In said distillation and/or separation unit 100, product components boiling at different temperature ranges and/or for special applications; gases 104, gasoline 101, diesel 102, and base oil 103, are separated.

DETAILED DESCRIPTION OF THE INVENTION

It has now been surprisingly found that branched saturated high-quality base oils are obtained by the process according to the invention, comprising an aldol condensation reaction of aldehydes and/or ketones containing heteroatoms, a hydrodeoxygenation reaction, and an isomerization reaction. In the process of the invention, the aldol condensation reaction of aldehydes and ketones, particularly of biological origin, may be utilized in combination with hydrodeoxygenation and the isomerization reactions the production of saturated base oils in a novel way.

In the aldol condensation reaction step the length of the hydrocarbon chain of the feedstock is increased to such that only carbon-carbon bonds are left in the basic structure of the molecule. Such aldehyde or ketone molecule is not suitable as such for base oil and therefore the oxygen present in the carbonyl group must be removed, and the low temperature properties must be improved for instance by making short branches to the molecular structure. Moreover, the process may optionally comprise a prehydrogenation step, recirculation and finishing steps of the product.

In case aldehydes and/or ketones, particularly of biological origin are used as the feedstock for producing base oils, it is necessary to increase the length of hydrocarbon chains thereof to obtain molecules having only carbon-carbon bonds in the basic structure. According to the invention, this is achieved by allowing aldehydes or ketones react with each other, thus producing carbon-carbon bonds in the molecule. In the structure of the products of the invention with increased hydrocarbon chain length, an aldehyde group is attached to a —$CH_2$— group in the middle of the long main hydrocarbon chain. If ketones are used as feed in the same condensation reaction, there are four longer hydrocarbon chains and a ketone group in on of these branches as shown in scheme (I). Also combinations of the two described reactions are possible. Aldehydes and ketones of the feedstock may also comprise two or several functional carbonyl groups, thus obtaining several branching sites in the structure of the product.

In the process of the invention aldehydes with carbon numbers from C1 to C40, preferably primary saturated aldehydes, and/or ketones with carbon numbers from C3 to C79, are reacted with each other in the condensation step. By this means the hydrocarbon chain length of the feedstock may be increased, and it reaches the carbon number of base oil. Also aldehydes and/or ketones with shorter chains may be used, thus enabling the increase of the molecular weight of the product by lower carbon numbers than by typical carbon numbers of fatty aldehydes ranging from C12 to C24 or typical for ketones ranging from C23 to C47, which enables the production of lighter compounds that base oil compounds. In a similar manner, aldehydes and/or ketones with two or more functional carbonyl groups may be used for lengthening the hydrocarbon chain. Said aldehydes with short chains and/or with two or more functional groups may be synthetic and/or derived from natural materials.

In the process of the invention, heteroatoms are removed from the product of the aldol condensation reaction in a hydrodeoxygenation step, thus liberating carbonyl oxygen in form of water. In addition, any other oxygen, nitrogen and sulfur compounds are simultaneously removed. Saturated branched hydrocarbons having branches in the middle of the chain are obtained as the product.

The product (mainly paraffins) obtained in the hydrodeoxygenation step is subjected to hydroisomerization. In the hydroisomerization the non-branched hydrocarbon chains of the molecules are isomerized so that they contain some more short branches, in order to improve low temperature properties. Following the hydroisomerization step, the oxidation stability of the product may be improved by an optional finishing treatment. In addition, an optional dewaxing may be performed prior to or after the finishing.

Branched paraffins with shorter chains of the diesel class are produced as by-products in the process.

Feedstock

The feedstock of the process comprises at least one aldehyde or ketone selected from the group consisting of C1-C40 aldehydes, C3-C79 ketones and C2-C40 hydroxy aldehydes, and mixtures thereof. Aldehydes and ketones of both synthetic and biological origin may be used as feedstock. C4-C24 fatty aldehydes, C3-C47 ketones and C4-C24 hydroxy aldehydes, preferably of biological origin, optionally subjected to one or more purification and/or conditioning step(s) of the prior art are preferably used. Conditioning steps include e.g. hydrolysis to produce fatty acids, transesterification with an alcohol or acid, esterification for producing fatty acid alkyl esters, reduction of fatty acids or fatty acid alkyl esters to give alcohols, as well as reduction of alcohols to give aldehydes, or ketonisation of fatty acids or fatty acid alkyl esters to give ketones.

The aldehydes and ketones may be produced using any known method in the art. Aldehydes and ketones are preferably produced from starting materials of biological origin, derived from plants, animals and fishes, and selected from the group consisting of plant oils, plant waxes, plant fats, animal oils, animal fats, animal waxes, fish oils, fish fats and fish waxes. Corresponding starting materials derived from algae and insects are also contemplated as well as starting materials derived from aldehydes and ketones prepared from carbohydrates.

The starting material of biological origin is suitably selected from the group consisting of:
a) plant fats, plant oils, plant waxes, animal fats, animal oils, animal waxes, fish fats, fish oils, fish waxes, and
b) free fatty acids or fatty acids obtained by hydrolysis, acid transesterification or pyrolysis reactions from plant fats, plant oils, plant waxes, animal fats, animal oils, animal waxes, fish fats, fish oils, fish waxes, and
c) esters obtained by transesterification from plant fats, plant oils, plant waxes, animal fats, animal oils, animal waxes, fish fats, fish oils, fish waxes, and
d) fatty acid alkyl esters obtained by esterification of alcohols with fatty acids of plant, animal and fish origin, and
e) alcohols and aldehydes obtained as reduction or hydrogenolysis products of free fatty acids, or fatty acids from plant fats, plant oils, plant waxes, animal fats, animal oils, animal waxes, fish fats, fish oils, fish waxes, and
f) ketones obtained by ketonisation reaction of the free fatty acids, esters, alcohols or aldehydes obtained from plant fats, plant oils, plant waxes, animal fats, animal oils, animal waxes, fish fats, fish oils, fish waxes, and
g) fatty alcohols obtained by hydrolysis, transesterification and pyrolysis from waxes of biological origin, and
h) waste and recycled food grade fats and oils, and fats, oils and waxes obtained by genetic engineering, and
i) mixtures of said starting materials.

Typical basic structural unit of plant and fish oils and animal fats is a triglyceride. Triglyceride is an ester of glycerol with three fatty acid molecules having the structure below:

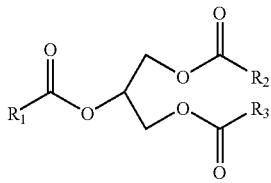

wherein $R_1$, $R_2$ and $R_3$ represent C4-C30 hydrocarbon chains. With respect to the hydrocarbon chain, said fatty acids are unbranched carboxylic acids with long chains. Main hydrocarbon chain lengths are 18 carbons (C18). C18 fatty acids are typically bonded to the middle hydroxyl group of glycerol. Fatty acids linked to the two other hydroxyl groups typically have even carbon numbers, generally between carbon numbers C14 and C22.

Fatty acid composition of the starting material of biological origin may considerably vary among feedstocks from different sources. While several double bonds may be present in fatty acids, they are non-conjugated, but at least one intermediate —$CH_2$— unit is between them. With respect to configuration, the double bonds of natural fatty acids are of cis form, hydrogen atoms being thus located on the same side of the rather rigid double bond. As the number of the double bonds increase, they are generally located at the free end of the chain. Lengths of hydrocarbon chains and numbers of double bonds depend on the various plant or animal fats, oils or waxes serving as the source of the fatty acid. Animal fats typically contain more saturated fatty acids than unsaturated fatty acids. Fatty acids of fish oil contain high amounts of double bonds, and the average length of the hydrocarbon chains is higher compared to fatty acids of plant oils and animal fats.

The fatty acid composition of the starting material of biological origin plays an important role in estimating oxidation resistance, thermal stability, and low temperature properties of the feedstock, and also in the determination of the types of products obtained by the aldol condensation reaction. Unsaturated components present in the feedstock readily undergo oligomerization, and also form compounds with ring structures, and following hydrogenation, result in more oligomeric hydrocarbons and hydrocarbons with ring structures in the final product.

Waxes are mainly fatty acids esterified with alcohols having long chains. Moreover, waxes contain various amounts of paraffins (n-alkanes), ketones, and diketones, primary and secondary alcohols, aldehydes, alkane acids (fatty acids) and terpenes. Carbon numbers of such fatty acid and alcohol chains are typically from C12 to C38.

Examples of suitable biological starting materials include fish oils such as baltic herring oil, salmon oil, herring oil, tuna oil, anchovy oil, sardine oil, and mackerel oil; plant oils such as rapeseed oil, colza oil, canola oil, tall oil, sunflower seed oil, soybean oil, corn oil, hemp oil, olive oil, cottonseed oil, mustard oil, palm oil, peanut oil, castor oil, jatropha seed oil, palm kernel oil, and coconut oil; and moreover, suitable are also animal fats such as lard, tallow, and also waste and recycled food grade fats and oils, as well as fats, waxes and oils produced by genetic engineering. In addition to fats and oils, suitable starting materials of biological origin include animal waxes such as bee wax, Chinese wax (insect wax), shellac wax, and lanoline (wool wax), as well as plant waxes such as carnauba palm wax, ouricouri palm wax, jojoba seed oil, candelilla wax, esparto wax, Japan wax and rice bran oil.

The process may also be used for processing mixtures of feeds originating from biological and synthetic materials, and if necessary, feedstocks produced by other processes, or synthetically produced feedstocks suitable for the process step in question may be used as additional feedstocks. Also pure synthetic feedstocks are contemplated, but in this case, the products are not based on renewable natural resources.

In addition to fatty aldehydes, also synthetic hydroxy aldehydes or hydroxy aldehydes derived from starting materials of biological origin may be used as feedstocks in the process of the invention. For the thermal stability of the base oil to be produced, preferably aldehydes and/or ketones free of tertiary carbon are used. Particularly for improving low temperature properties and for producing heavier base oils branched additional components to obtain branching sites in the structure of the base oils may be used.

Hydrocarbons serving as diluent, for instance hydrocarbons of the diesel class, preferably of biological origin, may optionally be added to the feedstock in different process steps. Boiling range of hydrocarbons of the diesel class is from 150 to 400° C., typically from 180 to 360° C.

Process

Condensation Step

Feedstock comprising at least one component selected from the group consisting of C1-C40 aldehydes, C3-C79 ketones, C2-C40 hydroxy aldehydes and mixtures hereof are subjected to condensation reaction. The aldehydes and/or ketones are condensed to substantially increase the carbon number of the hydrocarbon stream. Saturated aldehydes and ketones are preferably used as the feedstock. In the process, the aldol condensation reaction is preferably used, thus obtaining branched unsaturated aldehydes or ketones. In the condensation homogeneous or heterogeneous aldol condensation catalysts may be used. Supported alkali metal catalysts like $Na/SiO_2$ may be mentioned as heterogeneous catalysts.

The homogeneous catalyst is preferably an alkali or an alkaline earth metal hydroxide, for instance NaOH, KOH or $Ca(OH)_2$. The reaction temperature is from 80 to 400° C., preferably lower temperature is used with lower molecular weight feeds and higher temperatures with higher molecular weight feed. Optionally solvents such as alcohols may be used. The amount of the homogeneous catalyst to be used in the reaction varies from 1 to 20%, preferably from 1.5 to 19%, by weight. Alternatively, reaction conditions of the aldol condensation may be adjusted to yield hydroxy aldehydes such as aldols as the reaction products, thus minimizing the oligomerization based on the reaction of double bonds. In this case, also the hydroxyl group has to be removed as water in the next HDO step.

Hydrodeoxygenation Step

In the subsequent HDO step heteroatoms of the products obtained in the aldol condensation reaction are removed. In the HDO step of the process according to the invention, the product of the aldol condensation and hydrogen gas are reacted under a pressure ranging between 0.1 and 20 MPa, preferably between 1 and 15 MPa, the temperature being from 100 to 500° C., preferably from 150 to 350° C. In the HDO step, special catalysts containing a metal of the Group VIII and/or VIA of the periodic system of the elements, and alumina and/or silica may be used. The HDO catalyst is preferably a supported Pd, Pt, Rh, Ru, Ni, NiMo or CoMo catalyst, support being activated carbon, alumina and/or silica.

In a preferable embodiment, the reaction product obtained after the HDO step is purified for instance by stripping with steam, or with a suitable gas such as a light hydrocarbons, nitrogen or hydrogen. It is preferable for the process to remove impurities and water as efficiently as possible prior to the hydro isomerization step and/or finishing step.

Hydroisomerization Step

After the HDO and the optional purification steps, hydroisomerization is carried out by reacting hydrogen gas, the hydrogenated components, and optional paraffinic additional feed, in the presence of an isomerization catalyst. In the hydroisomerization step, the pressure ranges from 0.1 to 20 MPa, preferably from 1 to 15 MPa. The temperature ranges between 100 and 500° C., preferably between 200 and 400° C. In the hydroisomerization step, special catalysts containing molecular sieves and metals of the Group VIII of the periodic system of the elements, for instance Ni, Pt, and Pd, may be used. Alumina and/or silica may be used as supports.

Prehydrogenation Step

The feedstock, as well as the product from the aldol condensation reaction may be subjected to an optional prehydrogenation step under mild conditions to hydrogenate possible double bonds and to reduce coke formation in the next process step since catalytic activity is mainly lost due to coal formation on the surface thereof. The prehydrogenation is carried out in the presence of a hydrogenation catalyst at temperatures between 50 and 400° C., under a hydrogen pressure ranging from 0.1 to 20 MPa, preferably at temperatures between 150 and 300° C., under a hydrogen pressure ranging from 1 to 10 MPa. The prehydrogenation catalyst contains metals of the Group VIII and/or VIA of the periodic system of the elements. The prehydrogenation catalyst is preferably a supported Pd, Pt, Ni, Ru, Rh, Cu, CuCr, NiMo or CoMo catalyst, the support being either activated carbon, alumina and/or silica.

Dewaxing Step

Following the hydroisomerization step, optional dewaxing step may be performed either catalytically or as solvent-based dewaxing. In the catalytic dewaxing, hydrogen gas and the component to be isomerized, as well as optional paraffinic additional feed react in the presence of a dewaxing catalyst. Zeolite catalysts comprising metals of the Group VIII of the periodic system of the elements such as Ni, Pt or Pd are used. In the dewaxing step, the pressure varies from 0.1 to 20 MPa, the temperature being between 100 and 500° C.

In the solvent-based dewaxing, paraffinic waxes are separated by dissolving the oil in a mixture of solvents, for instance methylethyl ketone and toluene. In the process, the solvent and the feed are passed counter current and thus mixed. The mixture of oil (isomerized product) and solvent is introduced to a cooling unit. Cooling results in crystallization of the paraffinic waxes. The cooling temperature depends on the desired low temperature properties of the product. Wax crystals are filtered from the mixture, collected for further processing, and the solvent is separated by evaporation from the base oil.

Finishing Step

The product obtained above may optionally be finished for removing any double bonds and aromatics. In case said finishing is performed using hydrogen in the presence of a catalyst, it is called hydrofinishing, the pressure thus ranging from 1 to 20 MPa, preferably from 2 to 15 MPa, and the temperature ranges between 50 and 500° C., preferably between 200 and 400° C. In the hydrofinishing, special catalysts containing metals of the Group VIII of the periodic system of the elements, and alumina and/or silica may be used. The hydrofinishing catalyst is preferably a supported Pd, Pt, or Ni catalyst, the support being alumina and/or silica. Finishing may also be achieved by removing polar components using adsorption materials, such as clay or molecular sieves.

Following the optional finishing, the product is passed to a distillation and/or separation unit for separating product components boiling over different temperature ranges and/or intended for different applications.

If desired, the hydrocarbon component obtained as the product, or another suitable hydrocarbon may be used as diluent in various stages of the process of the invention, such as in the aldol condensation, HDO and/or isomerization steps for increasing the conversion and/or selectivity and/or for controlling the exothermal nature of the reactions.

A fixed catalyst bed reactor, for instance the trickle-bed reactor of the prior art is preferably used in prehydrogenation, HDO, hydroisomerization, and hydrofinishing steps.

Product

The process according to the invention yields a high quality branched and saturated hydrocarbon component suitable as base oil. The base oil product has excellent viscosity and low temperature properties. The process according to the invention also yields as by-product paraffinic hydrocarbon product suitable for diesel fuel pool. The diesel component contains typically some short carbon-carbon side branches, resulting in an exceptionally low cloud point and cold filter plugging point but still a good cetane number. In addition, a hydrocarbon component suitable as a solvent, gasoline and/or a component of gasoline is obtained as by-product. All these products are preferably of biological origin.

Feedstocks, and preferably feedstocks derived from biological starting materials have a substantial effect on the composition and distillation range of the product. Components of feedstocks derived from fatty acids may be fractionated by distillation to give fractions having narrow carbon number ranges to be tailored according to requirements of various applications. For feedstocks having hydrocarbon chains of C16, C18, C20 and C22, typical carbon numbers of the products are respectively C32, C36, C40, and C44. Product fractions having narrow carbon number ranges and distillation ranges are obtained since the distillation range of the product mainly depends on the length of the hydrocarbon chain of the feedstock. Base oils with narrow distillation ranges obtained according to the invention have extremely low volatilities when compared to corresponding products of the prior art.

Carbon number ranges of the base oils of the invention are extremely narrow, typically no more than 5 carbons wide for C12/C14, C14/C16 and C16/C18 feedstocks. Most typical structures and carbon number ranges of the base oils produced by the process of the invention (with kinematic viscosity of 4-6 cSt/100° C.) are presented in Table 2. The carbon number is governed by the carbon number of the feedstock. Most typical carbon numbers are shown bold-faced. Typical structures and carbon number ranges (C25-C35) of synthetic hydroisomerized hydrocarbon base oils VHVI, GTL and Slack Wax base oils of the prior art, derived from mineral oils, and belonging to the same viscosity class (about 4 to 6 cSt/100° C.), are also presented in Table 2.

TABLE 2

Carbon numbers and structures of base oils

| Base oil | Carbon number/%, by FIMS | Structure |
|---|---|---|
| 1<br>Derived from aldehyde | C32/C34/C36<br>acyclic component about 90%<br>mononaphthenes about 10% | 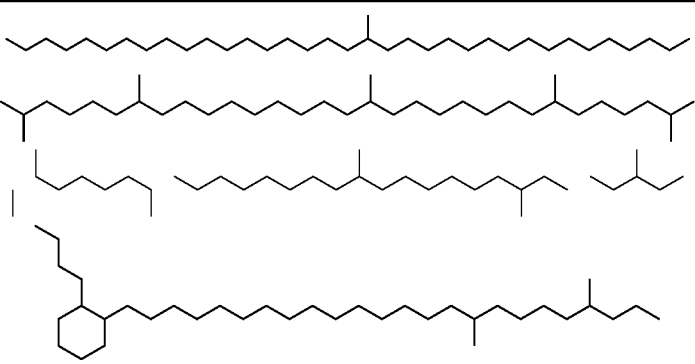 |
| 2<br>Derived from aldehyde and ketone | C33/C37/C41/C45<br>acyclic component about 90%<br>mononaphthenes about 10% | 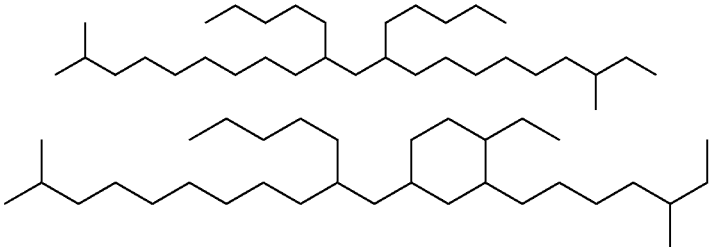 |
| 3<br>Derived from ketone | C46/C54/C62/C70<br>acyclic component about 90%<br>mononaphthenes about 10% | 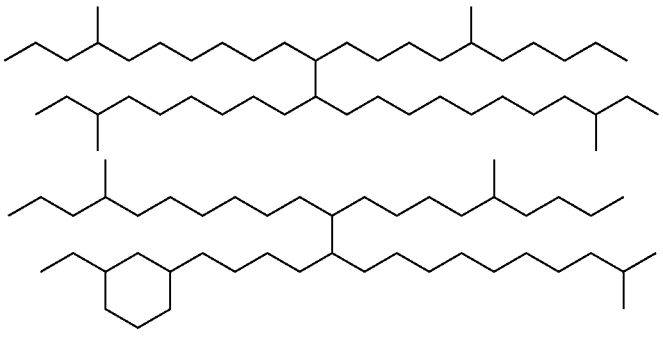 |
| 4<br>GTL | C25-C35<br>acyclic component about 90%<br>mononaphthenes about 10% | 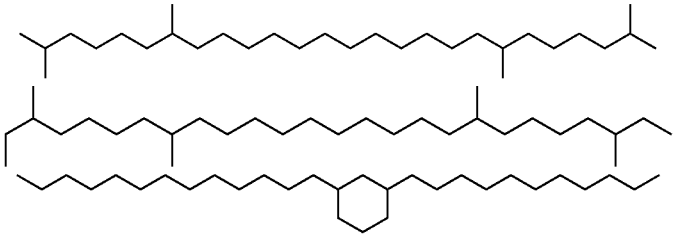 |

TABLE 2-continued

Carbon numbers and structures of base oils

| Base oil | Carbon number/%, by FIMS | Structure |
|---|---|---|
| 5 Slack Wax (SW) | C25-C35 acyclic component about 70% mononaphthenes about 25% dinaphthenes about 5% | 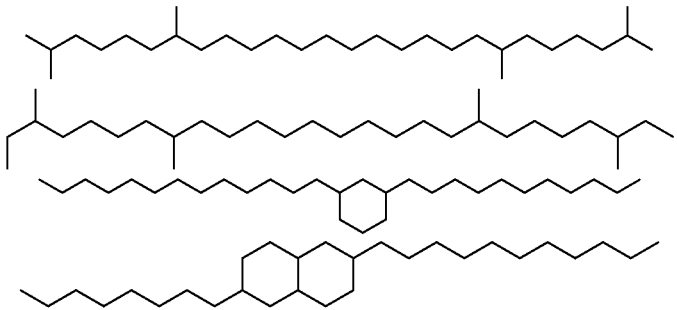 |
| 6 VHVI | C25-C35 acyclic component about 40% mononaphthenes about 35% dinaphthenes about 15% other naphthenes about 10% | 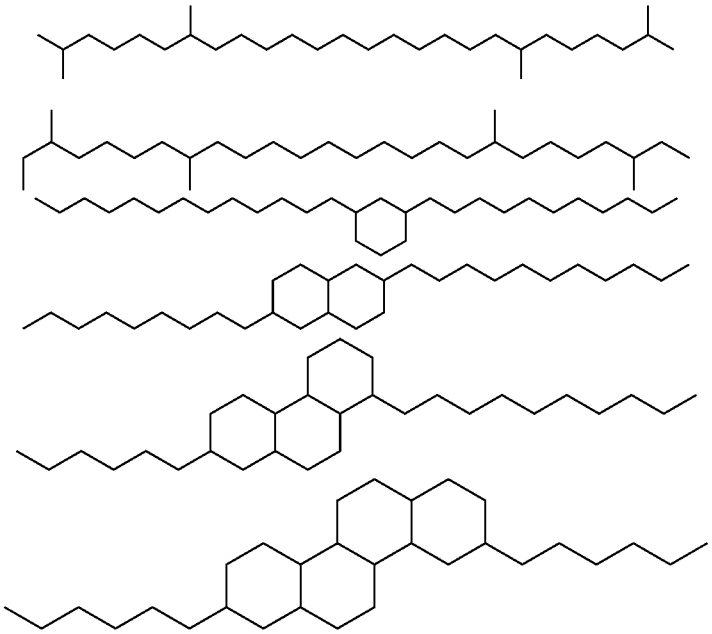 |

Base oils shown in Table 2 are produced as follows:

1. Base oil of the invention is obtained by aldol condensation, hydrogenation and hydroisomerization of feed comprising C18 aldehyde.

2. Base oil of the invention is obtained by aldol condensation, hydrogenation and hydroisomerization of feed comprising C23 ketone and C5 aldehydes.

3. Base oil of the invention is obtained by aldol condensation, hydrogenation and hydroisomerization of feed comprising C23 ketone.

4. GTL is an isomerization product of the Fischer-Tropsch waxy fraction.

5. SW is an isomerization product of the Slack Wax waxy fraction, derived from mineral oil.

6. VHVI is a hydrocracked and isomerized base oil derived from mineral oil.

Saturated hydrocarbons are classified according to the carbon and hydrogen atoms by field ionization mass spectrometry (FIMS) method as follows:

| 1 | $C(n) \cdot H(2n+2)$ | paraffins |
| 2 | $C(n) \cdot H(2n)$ | mononaphthenes |
| 3 | $C(n) \cdot H(2n-2)$ | dinaphthenes |
| 4 | $C(n) \cdot H(2n-4)$ | trinaphthenes |
| 5 | $C(n) \cdot H(2n-6)$ | tetranaphthenes |
| 6 | $C(n) \cdot H(2n-8)$ | pentanaphthenes |

In Table 2, the percentages (%, by FIMS) refer to the groups of compounds determined according to said method.

Using feedstocks with different hydrocarbon chains lengths and the aldol condensation reaction, molecular masses of the products may be increased to reach viscosity ranges required for different applications. In the condensation reaction the length of the hydrocarbon chain of the feedstock is increased. It is thus possible to produce lighter hydrocarbon products such as solvents, gasoline, and diesel fuels from feedstocks with shorter chains, and base oils from feedstocks with longer chains.

With respect to molecular structure, base oils of the invention differ from products of the prior art as may be seen from Table 2. The product obtained by the process according to the invention using aldehydes as feed compounds comprises a methyl branch in the middle of the main hydrocarbon chain (structure 1 in Table 2). The product differs from the GTL and SW isomerization products of the prior art (structures 4 and 5 in Table 2) typically having branches only at the ends of the chains. If aldehydes and ketones are used as feed compounds, the product obtained with the process of the invention has remarkably longer side chains compared to products of the prior art (structures 4 and 5 in Table 2). And finally, if ketones are used as feed compounds, the product obtained with the process of the invention has even longer side chains compared to products of the prior art (structures 4 and 5 in Table 2).

Branches located in the middle of the hydrocarbon chain lower the pour point considerably more than those at the ends of the chain. In addition to the location of the branches, the number thereof affects the pour point, it being lowered by increasing branching, but at the same time also the viscosity index is reduced. Accordingly, being favourable for both the pour point and the viscosity index, the number of the branches should be limited. The product obtained by isomerization of the paraffinic wax from the aldol condensation reaction (structures 1-3 in Table 2) has methyl branches at the ends of the hydrocarbon component, and to a lesser extent ethyl branches within the hydrocarbon chain, and in addition a branch or branches in the middle of the main hydrocarbon chain.

There exists an optimum correlation between the viscosity index and pour point with the main hydrocarbon chain comprising only a few branches. Accordingly, to improve the pour point, the paraffin with some branches requires less isomerization in the process of the invention after the HDO step in comparison to paraffinic waxes completely free of branches of the prior art. Typically the products of the invention comprise relatively high proportions of isomerized molecules containing more than 30 carbon atoms. Such branched high molecular weight compounds typically also exhibit high viscosity indices (VI) even though pour point is below −20° C.

The base oil according to the invention comprises branched hydrocarbons having carbon number at least C18, and it comprises at least 90%, preferably at least 95%, and particularly preferably at least 97% by weight of saturated hydrocarbons (GC). Preferably the base is of biological origin and produced from starting materials of biological origin. It comprises not more than 15% by weight, preferably not more than 10% by weight and particularly preferably not more than 5% by weight of mononaphthenes (FIMS). It comprises not more than 1% by weight, preferably not more than 0.5% by weight and particularly preferably 0.1% by weight of fused dinaphthenes and polynaphthenes (FIMS).

For base oils according to invention the viscosity index is more than 120, preferably at least 130 and particularly preferably at least 140 (ASTM D 2270) and pour point is lower than −9° C., preferably lower than −12° C. and particularly preferably lower than −15° C. (ASTM D 5950).

Width of the carbon number range of base oils of the invention is no more than 5 carbons, preferably no more than 3 carbons, and particularly preferably no more than 1 carbon (FIMS). At least 60% by weight of the saturated hydrocarbons are within the specified carbon number range (of no more than 5, etc.) preferably at least 75% by weight and particularly preferably at least 90% by weight.

Distillation range of base oils of the invention is no more than 150° C., preferably no more than 100° C., particularly preferably no more than 70° C. (determined by the method of ASTM D 2887, distillation points D10 and D90).

Sulfur content of base oils of the invention is less than 300 ppm, preferably less than 50 ppm, and particularly preferably less than 1 ppm (ASTM D 3120).

Nitrogen content of base oils of the invention is less than 100 ppm, preferably less than 10 ppm, and particularly preferably less than 1 ppm (ASTM D 4629).

For the base oil or base oil component, the volatility of product, having KV100 from 3 cSt to 8 cSt, is no more than $2271.2*(KV100)^{-3.5373}$% by weight as determined by the method of DIN 51581-2 (Mathematical Noack method based on ASTM D 2887 GC distillation).

Base oils of the invention, based on biological starting materials, contain carbon $^{14}C$ isotope, which may be considered as an indication of the use of renewable raw materials. Typical $^{14}C$ isotope content (proportion) of the total carbon content in the product, which is completely of biological origin, is at least 100%. Carbon $^{14}C$ isotope content is determined on the basis of radioactive carbon (carbon $^{14}C$ isotope) content in the atmosphere in 1950 (ASTM D 6866). $^{14}C$ isotope content of the base oil according to the invention is lower in cases where other components besides biological components are used in the processing of the product, said content being, however, more than 50%, preferably more than 90%, particularly preferably more than 99%. In this way, even low amounts of base oil of biological origin may be detected in other types of hydrocarbon base oils.

ADVANTAGES OF THE INVENTION

The process of the invention particularly allows for the use of renewable starting materials of biological origin, containing heteroatoms, for producing base oils derived from renewable natural resources, but also diesel and gasoline components as by-products. In addition to traditional crude oil, a completely new raw material source for high-quality branched paraffinic base oils is provided according to the invention. Also carbon dioxide emissions contributing to the greenhouse effect may be reduced by using renewable raw material sources instead of non-renewable ones.

According to the invention, a base oil only containing carbon and hydrogen is obtained, the stability of said base oil in humid conditions being higher than that of base oils containing esters or other heteroatoms. A paraffinic hydrocarbon component is not decomposed as easily as esters that form corrosive acids. A non-polar and fully saturated branched hydrocarbon component, free of sulfur is obtained using the process of the invention. Oxygen and heteroatoms of any impurities of the feedstock are removed in the HDO step.

In the isomerization step, the carbon chain is branched, thus improving low temperature properties, that is, the pour point is lowered and filterability at low temperatures is improved. Wax is converted to oily hydrocarbon having a viscosity index (viscosity-temperature-dependence) very suitable for base oil without any blending limitations, and further it is fully compatible with lubricant additives.

High hydrogen partial pressure and low levels of impurities may be maintained throughout the whole process. Carbon monoxide, carbon dioxide and water contents may thus be lowered to the extent that light stripping in the HDO stage or in a separate gas/liquid separation vessel is sufficient to remove residual impurities prior to isomerization. By means of the optional prehydrogenation step, yield may be improved and side reactions e.g. polymerization, ring formation, and aromatization of the double bonds of hydrocarbon chains resulting in coke formation on the catalyst surface, and reduction of the operation time may be reduced. Also the viscosity properties of the base oils are changed by ring formation and polymerization.

With the process of the invention, high-quality saturated base oils having low pour points may be produced, said base oil being thus very useful at low temperature conditions. The product is typically free of sulfur, the viscosity index thereof being preferably at least 120, and thus it may also be suitably used in applications of Group III base oils.

Fatty aldehydes and ketones derived from fatty acids, which are distilled to fractions according to carbon numbers may be used as feedstocks. According to the invention branched paraffinic base oils having narrow boiling ranges and various physical properties may be processed from these fractions. Typical carbon number ranges of the product components are as follows: gas C1-C4, gasoline C5-C10, diesel C11-C26, base oil at least C18. Distillation range of base oils produced from a feedstock having a single carbon number is narrow.

Narrow distillation range indicates that the product does not contain any initial light fraction (meaning molecules considerably lighter than the average), seen as decreased volatility of the product and resulting in reduced emissions and reduced use of lubricants in practical applications. Neither any "tail" composed of the heavier components (meaning molecules considerably heavier than the average), are contained in the product, resulting in excellent low temperature properties of the product.

For the base oil of the invention, the carbon number and distillation range are governed by the feedstock composition. For base oils of the prior art, the distillation range is adjusted by distilling the product to obtain a fraction having the desired kinematic viscosity. It is preferable for the lubricants to have base oils with narrow carbon number ranges and thus narrow distillation ranges. Therefore, the compositions of base oils according to the invention contain molecules of similar sizes behaving in a similar way under different conditions.

The base oil according to the invention has high viscosity index, which leads to a significantly decreased need of high price Viscosity Index Improver (VII) or in other terms Viscosity Modifier (VM). It is commonly known, that the VII is an additive, which causes highest amount of deposits in vehicle engines. In addition, reduction of the amounts of VII results in significant savings in costs.

Also, because the base oil is non-toxic, contains no sulfur, nitrogen or aromatic compounds typically present in the conventional mineral oil based products, it may more safely be used in applications where the end user is exposed to oil or oil spray.

Moreover, response of the base oil according to the invention is extremely high for antioxidants and pour point depressants, and thus the life time of the lubricating oils are longer and they can be used in the colder environment than lubricants based on the conventional base oils.

The base oil of the invention is also chemically more stable than products based on more reactive esters, and the oxidation resistance thereof is better than that of base oils based on fatty acids or fatty alcohol dimers, or base oils based on esters, produced from unsaturated fatty acids of biological origin.

Compared to esters, the base oil of the invention is more compatible with conventional base oils derived from crude oil, base oils obtained from Fischer-Tropsch process, and with hydrocarbon base oils, as well with lubricant additives. Moreover, it is compatible with elastomers, and thus it can be used in modern vehicle engines without modifications.

An additional advantage of the base oil according to this invention is that it fulfils the API group III base oil specifications. Therefore it can be used in engine oil formulations like other group III base oils according the same interchanging rules without need to perform new engine tests.

The base oil of the invention is preferably based on renewable natural resources. Starting materials of the process of the invention are available all over the world, and moreover, the utilization of the process is not limited by significant initial investments in contrast for instance to the GTL technology.

The products of the inventive process are carbon dioxide neutral with respect to the use and disposal thereof, that is, they will not increase the carbon dioxide load of the atmosphere in contrast to products derived from fossil starting materials.

At least one methyl branch is found in the middle of the main hydrocarbon chain in the hydrocarbon component produced by the process of the invention. Such C11-C26 hydrocarbons with at least one methyl branch of the diesel class, produced from C5-C13 feedstocks, have superior low temperature properties, that is, they are liquid even at low temperatures, the cloud point being low. In contrast, for heavier C26-C40 hydrocarbon components and for base oil applications, more than one branch is necessary, said branches being obtained mainly by hydroisomerization.

The properties of the hydrocarbon components produced with the process according to the invention are excellent. The products are well suited as base oils without blending limitations, and further, the products are also compatible with lubricant additives.

EXAMPLES

The invention is now illustrated in more detail with the following examples. It is however clear that the invention is not limited to embodiments described in the examples. The invention may also be carried out in other ways without departing from the invention.

Example 1

Preparation of a Hydrocarbon Component from C16 Aldehyde

In aldol condensation reaction 200 g of C16 fatty aldehyde derived from palm oil and 100 g of 20% NaOH dissolved in water were put in a Parr reactor. Mixing was adjusted to 250 rpm, temperature to 250° C. and pressure to 0.5 MPa. Slight nitrogen purge was maintained to sweep out water liberated in reaction. Reaction was carried out until the amount of condensed aldehyde was stabilised in GC analysis. After the reaction the product was neutralized with hydrochloric acid, washed with water and dried with calcium chloride.

In the next HDO step, the condensed aldehyde obtained above was hydrogenated in a high pressure Parr reactor using a dried and activated $NiMo/Al_2O_3$ catalyst, to give a methyl branched paraffin. The aldehyde was hydrogenated at 340° C., under a pressure of 5 MPa, mixing at 300 rpm until no aldehyde peak was detected in the FTIR spectrum. The pour point of the obtained methyl branched C32 paraffin wax was 69° C.

Example 2

Preparation of a Hydrocarbon Component from C23 Ketone and Furfural

In the aldol condensation step 14.6 g laurone (C23 ketone derived from palm kernel oil), 150 ml isopropanol and 15 ml of 10% NaOH in water was mixed and refluxed 20 min in a round bottom flask at 80° C. 15 g of furfural (aldehyde derived from aldohexose sugar) was added and heating under reflux was continued for 5 hours. After cooling, alcohol was evaporated in a rotary evaporator. Reaction was repeated and residues from two syntheses were dissolved in ethyl acetate, cooled in ice and the unreacted laurone was filtrated from cold solution.

In the next HDO step, the condensation product obtained above was hydrogenated in a high pressure Parr reactor using a dried and activated NiMo/Al$_2$O$_3$ catalyst, to give a methyl branched paraffin. The aldehyde was hydrogenated at 320° C., under a pressure of 5 MPa, mixing at 300 rpm for 5 hours. The pour point of the obtained pentyl branched wax was 11° C.

Example 3

Preparation of a Hydrocarbon Component from Ketones Derived from Plant Oil

In the aldol condensation step 10 g of C31/C33/C35 ketone mixture derived from palm oil fatty acids and 2 g of NaOH were heated in a round bottom flask to 400° C. for 30 min under mixing. After cooling the synthesis product was dissolved in 50 ml of ethyl acetate, filtrated and the diluent was evaporated.

In the next HDO step, the condensation product obtained above was hydrogenated as in Example 2. The pour point of branched wax was 35° C.

Example 4

Hydroisomerization

The C32 paraffin wax obtained in Example 1 was isomerized in a Parr reactor to give a branched paraffin of the base oil class using a reduced Pt molecular sieve/Al$_2$O$_3$ catalyst. Preheated paraffin was isomerized under a hydrogen pressure of 3 MPa and at 340° C. until a pour point under −15° C. was obtained. Finally, light fractions were distilled from the product at reduced pressure.

Properties of the base oil obtained in example 4 are presented in following Table 3 as well as properties of prior art products.

TABLE 3

Base oil according to example 4 and prior art products.

|  |  | Examp. 4 | API GpIII VHVI | API GpIII SW | API GpIII GTL |
|---|---|---|---|---|---|
| FIMS | average MW | 451 | 400 | 397 | 410 |
|  | PARAFFINS | 90 | 37 | 72 | 95 |
|  | MONONAPHTHENES | 9.5 | 37 | 24 | 5 |
|  | DINAPHTHENES | 0.5 | 16 | 3.5 | 0 |
|  | OTHER NAPHTHENES | 0 | 10 | 0.5 | 0 |
| Base oil properties | PP ° C. (ASTM D5950) | −26 | −18 | −21 | −21 |
|  | VI (ASTM D2270) | 145 | 122 | 140 | 139 |
|  | KV100 cSt (ASTM D445) | 4.3 | 4.3 | 4.0 | 4.1 |
| GC distillation ASTM D2887 | D10, ° C. | 390 | 395 | 394 |  |
|  | D50, ° C. | 444 | 421 | 421 |  |
|  | D90, ° C. | 455 | 456 | 459 |  |
| Noack volatility, wt-% | (DIN 51581-2) | 11.1 | 13.3 | 12.5 |  |

C1-C40 aldehydes and/or C3-C79 ketones, C2-C40 hydroxy aldehydes and mixtures thereof are suitable as feedstock. Aldehydes and/or ketones of both synthetic and biological origin may be used. C4-C24 fatty aldehydes and/or C7-C47 ketones of biological origin, optionally subjected to one or more purification and/or conditioning step(s) of the prior art being preferably used.

The invention claimed is:

1. Process for producing base oil, characterized in that
    a) feedstock comprising at least one aldehyde and/or ketone selected from the group consisting of C1-C40 aldehydes, C3-C79 ketones, C2-C40 hydroxy aldehydes and mixtures thereof, is condensed in the presence of an aldol condensation catalyst at temperature ranging from 80 to 400° C. to obtain a condensation product comprising branched unsaturated aldehydes, ketones, or hydroxy aldehydes, respectively,
    b) the condensation product is hydrodeoxygenated in the presence of a hydrodeoxygenation catalyst under a hydrogen pressure ranging from 0.1 to 20 MPa at a temperature ranging from 100 to 500° C. to obtain paraffins, and then
    c) the paraffins are hydroisomerized in the presence of an isomerization catalyst under a hydrogen pressure ranging from 0.1 to 20 MPa at a temperature ranging from 100 to 500° C. to obtain base oil, wherein said base oil comprises:
        i. branched hydrocarbons having carbon numbers of at least C18,
        ii. at least 90% by weight of saturated hydrocarbons,
        iii. mononaphthenes not more than 15% by weight
        iv. fused dinaphthenes and polynaphthenes not more than 1% by weight,
        v. at least 60% by weight of the saturated hydrocarbons are within the carbon number range of no more than 5.

2. The process according to claim 1, characterized in that the feedstock comprises at least one feed component selected from the group consisting of C4-C24 fatty aldehydes, C3-C47 ketones and C4-C24 hydroxy aldehydes and mixtures thereof.

3. The process according to claim 2, characterized in that said feed component is derived from a starting material of biological origin selected from the group consisting of plant oils, plant waxes and plant fats; animal oils, animal fats and animal waxes; fish oil, fish fats and fish waxes; recycled food grade fats and oils; fats, oils and waxes obtained by genetic engineering; oils and fats derived from algae and insects; aldehydes and ketones prepared from carbohydrates by acid hydrolysis process, and mixtures of said starting materials.

4. The process according to claim 1, characterized in that the aldol condensation catalyst is alkali or alkaline earth metal hydroxide.

5. The process according to claim 1, characterized in that hydrodeoxygenation is performed under hydrogen pressure ranging from 1 to 15 MPa at a temperature ranging from 150 to 350° C.

6. The process according to claim 1, characterized in that the hydrodeoxygenation catalyst contains at least one component selected from the group consisting of metals of the Group VIII or Group VIA of the periodic system of the elements, and support, activated carbon, alumina and/or silica.

7. The process according to claim 1, characterized in that hydroisomerization is performed under a hydrogen pressure ranging from 1 to 15 MPa at a temperature ranging from 200 to 400° C.

8. The process according to claim 1, characterized in that the hydroisomerization catalyst comprises a metal of the Group VIII of the periodic system of the elements, a molecular sieve and/or a support, said support being alumina and/or silica.

9. The process according to claim 1, characterized in that prior to the condensation, prehydrogenation is carried out under a hydrogen pressure between 0.1 and 20 MPa, and at a temperature between 50 and 400° C., in the presence of a prehydrogenation catalyst.

10. The process according to claim 9, characterized in that the prehydrogenation catalyst contains supported metals of the Group VIII and/or VIA of the periodic system of the elements, the said support being activated carbon, alumina and/or silica.

11. The process according to claim 1, characterized in that hydrocarbon or a mixture of hydrocarbons is added to the feedstock and/or as a diluent to process steps.

12. The process according to claim 6, characterized in that the metal is Pd, Pt, Rh, Ru, Ni, NiMo or CoMo.

13. The process according to claim 8, characterized in that the metal is Pd, Pt or Ni.

14. The process according to claim 9, characterized in that the hydrogen pressure is between 1 and 10 MPa, and the temperature is between 150 and 300° C.

15. The process according to claim 10, characterized in that the metal is Pd, Pt, Rh, Ru, Ni, Cu, CuCr, NiMo or CoMo.

* * * * *